United States Patent [19]

Klioze et al.

[11] 4,015,004
[45] Mar. 29, 1977

[54] PHENYLSULFENYLPIPERAZINES
[75] Inventors: Solomon S. Klioze; Richard C. Allen, both of Flemington, N.J.
[73] Assignee: American Hoechst Corporation, Bridgewater, N.J.
[22] Filed: Aug. 26, 1975
[21] Appl. No.: 607,927
[52] U.S. Cl. .................... 424/250; 260/268 PH; 260/268 S
[51] Int. Cl.² ................................... C07D 295/22
[58] Field of Search ............... 260/268 PH, 268 S; 424/250

[56] References Cited
UNITED STATES PATENTS 3,790,568  2/1974  Kerwood et al. ............... 260/268 S
3,887,571  6/1975  Gattuso ......................... 260/268 S

OTHER PUBLICATIONS

Pollard et al., J. Org. Chem., vol. 26, 600–601 (1961).
George de Steven et al., Chemical Abstracts, vol. 62, 11833 (1965).
Ozami Aki et al., Chemical Abstracts, vol. 77, 139,969f (1972).

Primary Examiner—Donald G. Daus
Assistant Examiner—Jose Tovar
Attorney, Agent, or Firm—Curtis, Morris & Safford

[57] ABSTRACT

Novel phenylsulfenylpiperazines and a method of preparing the same are disclosed. These compounds are useful as antihypertensive agents.

13 Claims, No Drawings

PHENYLSULFENYLPIPERAZINES

This invention relates to novel phenylsulfenylpiperazines which are useful as antihypertensive agents, to a method of preparing the same, to methods of treatment with pharmaceutically effective amounts thereof, and to pharmaceutical compositions containing such compounds as essential ingredients.

To the best of our knowledge, the compounds of this invention have not heretofore been described or suggested. Alkylthiomethylpiperazines and N-benzylthio-N'-phenylpiperazines described by C. B. Pollard et al. [J.O.C., 26, 600 (1961)] and Aki et al. [Chem. Pharm. Bull. 20, 1866 (1972)], respectively, are outside the scope of this invention.

This invention relates to novel phenylsulfenylpiperazines of the formula

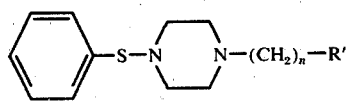

wherein n is the integer 0 or 1 and R' is pyridyl, phenyl or phenyl substituted by halogen, lower alkyl or lower alkoxy (of 1 to 4 carbon atoms) or trifluoromethyl. Preferred compounds are those in which n equals 0.

The compounds of the present invention are prepared by the reaction of N-(phenylthio)phthalimide and an N-substituted piperazine of the formula

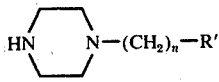

wherein n and R' are as defined earlier. Said reaction is carried out by preparing a mixture of the reactants in a suitable organic solvent such as benzene and heating the reaction mixture to its reflux point.

It will be readily appreciated by those skilled in the art that the time necessary to complete the above reaction is dependent upon the particular N-substituted piperazine and the solvent.

The compounds of the invention are useful as antihypertensive agents due to their ability to depress blood pressure in mammals. Antihypertensive activity is measured in the spontaneous hypertensive rat by the indirect tail cuff method described, A. Schwartz, Ed., *Methods in Pharmacology*, Vol. I, page 135, Appleton-Century Crofts, New York, New York 1971. In this procedure a group of five animals is treated orally for three days with the drug in relation to a control group of the same number. The drop in blood pressure is measured on the third day following administration. The antihypertensive activities of some of the compounds, expressed as mm decrease in mean arterial blood pressure, are recited in Table I.

TABLE I

| Compound | dose (mg/kg of body weight) | mm Hg |
|---|---|---|
| 1-phenylpiperazine-4-phenylsufenamide | 25 | −90 |
| 1-(2-pyridyl)piperazine-4-phenylsulfenamide | 25 | −65 |
| 1-(2-methoxyphenyl)piperazine-4-phenylsulfenamide | 25 | −27 |
|  | 50 | −71 |
| 1-(4-chlorophenyl)piperazine-4-phenylsulfenamide | 50 | −44 |
| 1-(3-tolyl)piperazine-4-phenylsufenamide | 10 | −24 |
| 1-benzylpiperazine-4-phenylsulfenamide | 25 | −23 |

Compounds of the invention are useful as diuretic agents due to their ability to produce diuresis in mammals. Diuretic activity is measured in rats by a method described by C. M. Kagawa and M. J. Kalm, Arch. Intern. Pharmacodyn., 137, 241 (1962). Drugs are dosed orally to a group of rats and the average volume of urine excreted is divided by the average volume excreted by a positive control group of rats dosed orally with 1000 mg/kg of urea, a known diuretic agent. The resulting drug/urea ratio if greater than one are indicative of diuretic activity. For example, 1-(4-chlorophenyl)piperazine-4-phenylsulfenamide, exhibits a drug/urea ratio of 1.8 at a dose of 50 mg/kg.

The above data illustrate that the compounds of the present invention are useful for the treatment of hypertension and for producing diuresis when administered to mammals at doses of from 0.1 to 100 mg/kg of body weight.

Examples of other compounds of the invention include:

1-(4-propylphenyl)piperazine-4-phenylsulfenamide;
1-(3-ethoxyphenyl)piperazine-4-phenylsulfenamide;
1-(4-fluorophenyl)piperazine-4-phenylsulfenamide; and
1-(4-bromobenzyl)piperazine-4-phenylsulfenamide.

The compounds of the present invention may be administered to a patient by a convenient route such as orally, intramuscularly, intraveneously, subcutaneously or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% by weight of the unit. The amount of active compound in such compositions is such that a suitable dosage will be obtained. Preferred compositions and preparations according to the present invention are prepared so that an oral dosage unit form contains between 1 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings, and flavors. Materials used in preparing these various compositions must be pharmaceutically pure and non-toxic in the amounts utilized.

For the purpose of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The present invention is further illustrated by the following examples.

trate is evaporated in vacuo to provide a yellow oil which is triturated with an ether-petroleum ether mixture and cooled to yield a white crystalline solid. The solid is recrystallized from ethanol to give colorless crystals, mp 80°–82° C., of 1-(2-pyridyl)piperazine-4-phenylsulfenamide.

Analysis: Calculated for $C_{15}H_{17}N_3S$: 66.38%C; 6.31%H; 15.49%N; 11.82%S. Found: 66.27%C; 6.40%H; 15.78%N; 11.68%S.

By following the above manipulative procedure of Step B, 1-(3-trifluoromethylphenyl)piperazine is treated to produce 1-(3-trifluoromethylphenyl)piperazine-4-phenylsulfenamide.

EXAMPLE 2

A mixture of 3.53 g of 1-(3-tolyl)piperazine and 5.11 g of N-(phenylthio)phthalimide in 100 ml of benzene is heated at reflux under nitrogen for 17 hours, cooled to ambient temperature and filtered. The filtrate is evaporated in vacuo to a yellow solid which is recrystallized from ethanol to give pale yellow crystals, mp 44°–46° C., of 1-(3-tolyl)piperazine-4-phenylsulfenamide.

Analyis: Calculated for $C_{17}H_{20}N_2S$: 71.79%C; 7.09%H; 9.85%N; 11.27%S. Found: 71.98%C; 7.07%H; 10.08%N; 11.05%S.

EXAMPLES 3–10

An N-substituted piperazine of the formula

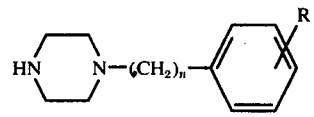

is reacted with N-(phenylthio)phthalimide according to the manipulative procedure described above in Example 2 to provide the compounds of the invention listed in Table II.

TABLE II

| | Starting Piperazine | | | Empirical | Analysis | | | | | | | |
| | | | | | Calculated | | | | Found | | | |
| Ex. | n | R | m.p.° C. | Formula | %C | %H | %N | %S | %C | %H | %N | %S |
|---|---|---|---|---|---|---|---|---|---|---|---|---|
| 3 | 0 | 4-methoxy | 96–98 | $C_{17}H_{20}N_2OS$ | 67.96 | 6.71 | 9.33 | 10.67 | 67.97 | 6.85 | 9.35 | 10.66 |
| 4 | 0 | 3-chloro | 65–67 | $C_{16}H_{17}N_2ClS$ | 63.04 | 5.62 | 9.19 | 10.52 | 63.14 | 5.39 | 9.41 | 10.45 |
| 5 | 0 | 2-methyl | 68–71 | $C_{17}H_{20}N_2S$ | 71.79 | 7.09 | 9.85 | 11.27 | 71.89 | 7.22 | 9.70 | 11.23 |
| 6 | 0 | 3-methoxy | 70–73 | $C_{17}H_{20}N_2OS$ | 67.96 | 6.71 | 9.33 | 10.67 | 67.89 | 6.71 | 9.55 | 10.72 |
| 7 | 0 | 2-chloro | 76–78 | $C_{16}H_{17}N_2ClS$ | 63.04 | 5.62 | 9.19 | 10.52 | 63.26 | 5.48 | 9.39 | 10.44 |
| 8 | 0 | H | 80–82 | $C_{16}H_{18}N_2S$ | 71.07 | 6.71 | 10.36 | 11.86 | 71.02 | 6.77 | 10.26 | 11.96 |
| 9 | 0 | 2-methoxy | 80–82 | $C_{17}H_{20}N_2OS$ | 67.96 | 6.71 | 9.33 | 10.67 | 68.03 | 6.81 | 9.26 | 10.46 |
| 10 | 1 | H | 86–89 | $C_{17}H_{20}N_2S$ | 71.79 | 7.09 | 9.85 | 11.27 | 71.66 | 7.16 | 9.84 | 11.07 |

EXAMPLE I

A. To a stirring solution of 29.4 g of phthalimide and 24 g of triethylamine in 80 ml of dimethylformamide is added dropwise under nitrogen a solution of 28.9 g of phenyl sulfenyl chloride in 120 ml of hexane. The reaction mixture is stirred for an additional 30 minutes, diluted with 800 ml of ice-water and filtered and the filtrate washed successively with water and petroleum ether to provide a nearly colorless crystalline solid. The solid is recrystallized twice from ethanol to provide fine nearly colorless crystals, mp 149°–152° C., of N-(phenylthio)phthalimide.

B. A mixture of 5.1 g of N-(phenylthio)phthalimide and 3.3 g of 1-(2-pyridyl)piperazine in 100 ml of benzene is heated at reflux under nitrogen for 17 hours, cooled to ambient temperature and filtered. The fil-

EXAMPLE 11

A mixture of 3.93 g of 1-(4-chlorophenyl)piperazine and 5.11 g of N-(phenylthio)phthalimide in 100 ml of benzene is heated at reflux for 18 hours, cooled to ambient temperature and filtered. The filtrate is evaporated in vacuo to provide a yellow solid which is recrystallized from ethanol to give fluffy colorless leaflets, mp 112°–120° C. These leaflets are chromatographed on a silica gel dry column using chloroform as the eluant. The appropriate band is excised and eluted with chloroform and the eluate evaporated in vacuo to provide a pale yellow solid which is recrystallized from ethanol to give fluffy colorless leaflets, mp 123°–125° C., of 1-(4-chlorophenyl)piperazine-4-phenylsulfenamide.

Analysis: Calculated for $C_{16}H_{17}N_2ClS$: 63.04%C; 5.62%H; 9.19%N; 10.52%S. Found: 63.19%C; 5.59%H; 9.34%N; 10.75%S.

We claim:

1. A compound of the formula

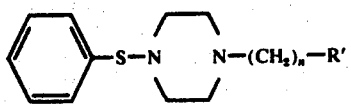

wherein $n$ is the integer 0 or 1 and R' is pyridyl, phenyl or phenyl substituted by halogen, lower alkyl, lower alkoxy or trifluoromethyl.

2. A compound as defined in claim 1 wherein $n$ is 0.

3. The compound as defined in claim 1 wherein R' is phenyl or phenyl substituted by halogen, lower alkyl, lower alkoxy or trifluoromethyl.

4. A compound as defined in claim 3 wherein $n$ is 0.

5. A compound as defined in claim 1 wherein R' is 2-pyridyl.

6. A compound as defined in claim 1 wherein R' is pyridyl, phenyl, methoxyphenyl, tolyl, chlorophenyl, bromophenyl, fluorophenyl or trifluoromethylphenyl.

7. The compound as defined in claim 5 which is 1-(2-pyridyl)piperazine-4-phenylsulfenamide.

8. The compound as defined in claim 3 which is 1-(3-tolyl)piperazine-4-phenylsulfenamide.

9. The compound as defined in claim 3 which is 1-phenylpiperazine-4-phenylsulfenamide.

10. The compound as defined in claim 3 which is 1-(4-chlorophenyl)piperazine-4-phenylsulfenamide.

11. A method of treating hypertension consisting essentially of administering to a patient a pharmaceutically effective amount of a compound defined in claim 1.

12. A method of producing diuresis consisting essentially of administering to a patient a pharmaceutically effective amount of a compound defined in claim 1.

13. A pharmaceutical composition consisting essentially of between 0.5 and about 70% by weight of a compound defined in claim 1 as an essential active ingredient, the balance being a pharmaceutically acceptable carrier therefor.

* * * * *